US009237983B2

(12) United States Patent
Milton

(10) Patent No.: US 9,237,983 B2
(45) Date of Patent: Jan. 19, 2016

(54) DUAL-PENETRATION SEX TOY FOR HETEROSEXUAL COUPLES

(71) Applicant: GGM Products, LLC, Brooklyn, NY (US)

(72) Inventor: Graham Milton, Brooklyn, NY (US)

(73) Assignee: GGM Products, LLC, Brooklyn, NY (US)

( * ) Notice: Subject to any disclaimer, the term of this patent is extended or adjusted under 35 U.S.C. 154(b) by 0 days.

(21) Appl. No.: 14/510,075

(22) Filed: Oct. 8, 2014

(65) Prior Publication Data

US 2015/0174001 A1 Jun. 25, 2015

Related U.S. Application Data

(60) Provisional application No. 61/888,371, filed on Oct. 8, 2013.

(51) Int. Cl.

| | |
|---|---|
| ***A61F 5/00*** | (2006.01) |
| ***A61H 19/00*** | (2006.01) |
| ***A61H 21/00*** | (2006.01) |
| ***A61H 9/00*** | (2006.01) |
| ***A61H 23/02*** | (2006.01) |

(52) U.S. Cl.

CPC .............. *A61H 19/50* (2013.01); *A61H 9/0078* (2013.01); *A61H 19/32* (2013.01); *A61H 19/34* (2013.01); *A61H 19/40* (2013.01); *A61H 19/44* (2013.01); *A61H 21/00* (2013.01); *A61H 23/02* (2013.01); *A61H 2201/0103* (2013.01); *A61H 2201/0111* (2013.01); *A61H 2201/165* (2013.01); *A61H 2201/1692* (2013.01); *A61H 2201/5097* (2013.01)

(58) Field of Classification Search

CPC ....... A61H 19/00; A61H 19/30; A61H 19/40; A61H 19/44

USPC ......................................... 600/38–41; 601/46

See application file for complete search history.

(56) References Cited

U.S. PATENT DOCUMENTS

| | | | | |
|---|---|---|---|---|
| 7,530,944 | B1 * | 5/2009 | Kain | 600/38 |
| 7,998,057 | B2 * | 8/2011 | Kain | 600/38 |
| 2014/0228629 | A1 * | 8/2014 | Baetica et al. | 600/38 |

* cited by examiner

*Primary Examiner* — John Lacyk

(74) *Attorney, Agent, or Firm* — Hunziker Legal Services; Will Hunziker

(57) ABSTRACT

A dual-penetration anal sex toy for couples is disclosed. For heterosexual couples, this toy is designed to enhance vaginal penetration with an anal-to-anal connection. A cock ring or means for attachment may fix the device against the wearer's perineum and act as a pivot-point to transfer the thrusting motion of the wearer directly to a prostate massaging butt plug. Because of the pivot point and possible simultaneous anal penetration both partners can feel a direct connection with the anal movements of the other.

19 Claims, 2 Drawing Sheets

DUAL-PENETRATION SEX TOY FOR HETEROSEXUAL COUPLES

BACKGROUND OF THE INVENTION

1. Field of the Invention

The present invention is in the technical field of sex toys. More particularly, the present invention pertains to the field of sex toys that are inserted into the body of two partners at the same time.

2. Description of Related Art

Sex toys have been around since the beginning of recorded history. As of 2013, the worldwide sex toy industry is estimated to be a $15 billion dollar a year industry with approximately 70% of the manufacturing being done in China. Common older types of penetrative sex toys include: dildos, Ben Wa balls, horseshoes, double penetration dildos, strap-on dildos, kegel exercisers, motorized sex machines, butt-plugs, anal beads, and prostate massagers; any of which can be fitted with vibrators. These sex toys are traditionally made of silicon, rubber, hard plastic, metal, glass, or cyber skin; although stranger materials can and are used.

More recently a product called a Feeldoe®, as described in U.S. Pat. No. 5,690,603, filed Jan. 22, 1996 has entered the market. The Feeldoe® allows a woman to insert one end into of the toy into her vagina thereby holding it in place while she uses the other end to penetrate her sexual partner; obviously, this design will not work well for a man and a woman. Other dual-pleasure toys, such as two-sided dildos either focus on vaginal penetration, or fail to transfer kinetic energy from one partner's anus to the other's. Likewise, strap-on dildos tend to focus on the sensations of the receiver and not the giver by butting the end of the dildo against the pubis, which has no erogenous sensitivity.

Until now, no sex toy has been developed that allows for a heterosexual couple to comfortably engage in simultaneous anal penetration while also performing normal vaginal intercourse.

SUMMARY

The scope of the present invention is defined solely by the appended claims and detailed description of a preferred embodiment, and is not affected to any degree by the statements within this summary. In addressing many of the problems experienced in the related art, such as those relating to the Feeldoe®, embodiments of the present disclosure presents a sex toy preferably designed to enhance penile to vaginal penetration in a missionary position with an anal-to-anal connection between the two partners. This may be accomplished by inserting one end of the sex toy into the anus of the wearer and using a cock ring or strap to fix the sex toy against the wearer's perineum by hooping over the wearer's penis, or strap-on, thereby creating a pivot-point which allows the wearer to transfer the motion of their thrusting directly back into their anal cavity. This design allows for a woman to receive vaginal and anal penetration, while the wearer is simultaneously being penetrated anally. Because of the pivot point and simultaneous anal penetration both the wearer and the receiver can feel a direct connection with the anal movements in their partner.

Additional embodiments of the description allow for the use of vibrators, waterproofing, rechargeable batteries, charging platforms, control systems to modulate vibration patterns, and bladders filled with air or fluid that allow for expansion or retraction of various parts of the sex toy.

BRIEF DESCRIPTION OF THE DRAWINGS

The above, and other, aspects, features, and advantages of several embodiments of the present disclosure will be more apparent from the following Detailed Description as presented in conjunction with the following several figures of the Drawing.

FIGURES

Figure 1:
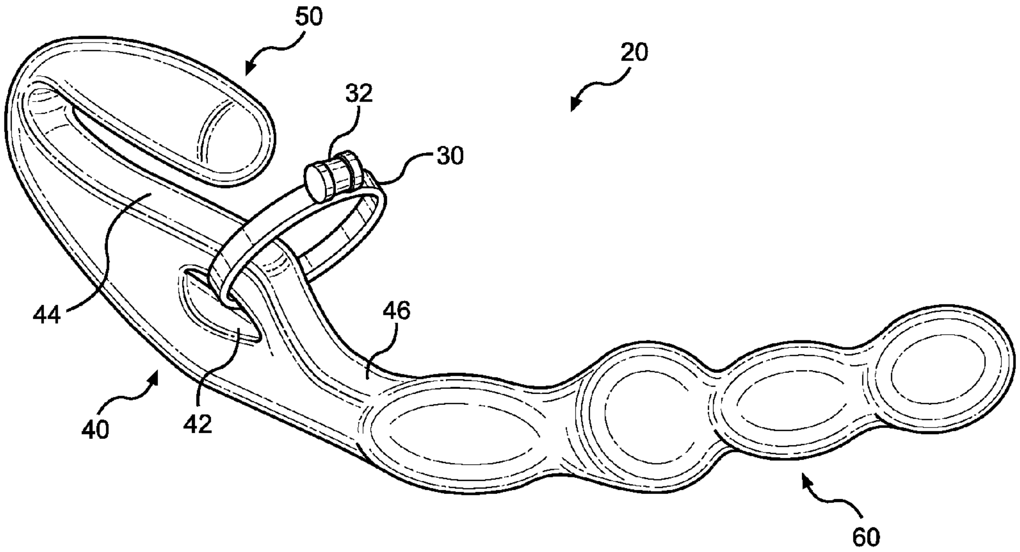

FIG. 1 (Sheet 1) illustrates a perspective view of a sex toy, in accordance with an embodiment of the present disclosure.

Figure 2:
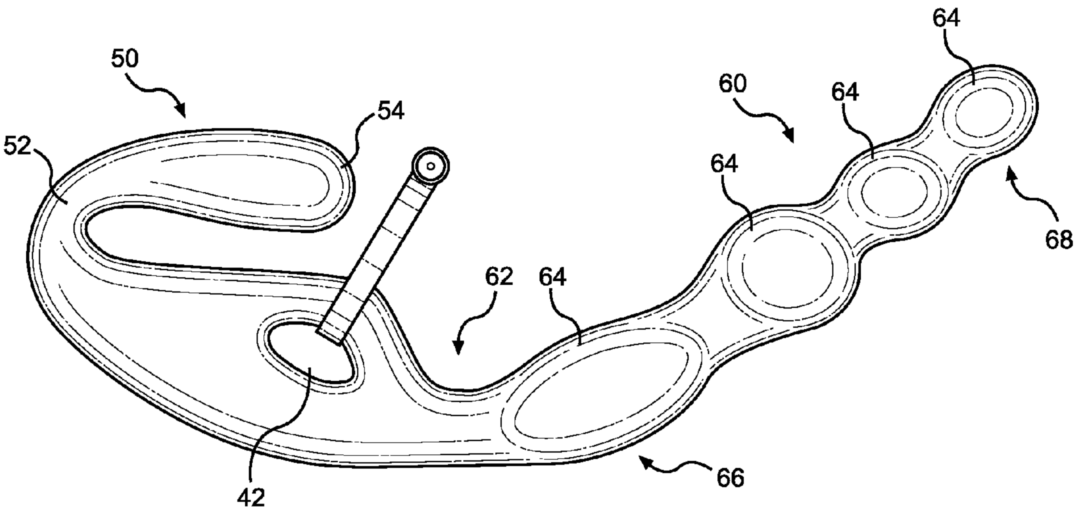

FIG. 2 (Sheet 1) illustrates a side view of a sex toy, in accordance with an embodiment of the present disclosure.

Figure 3:
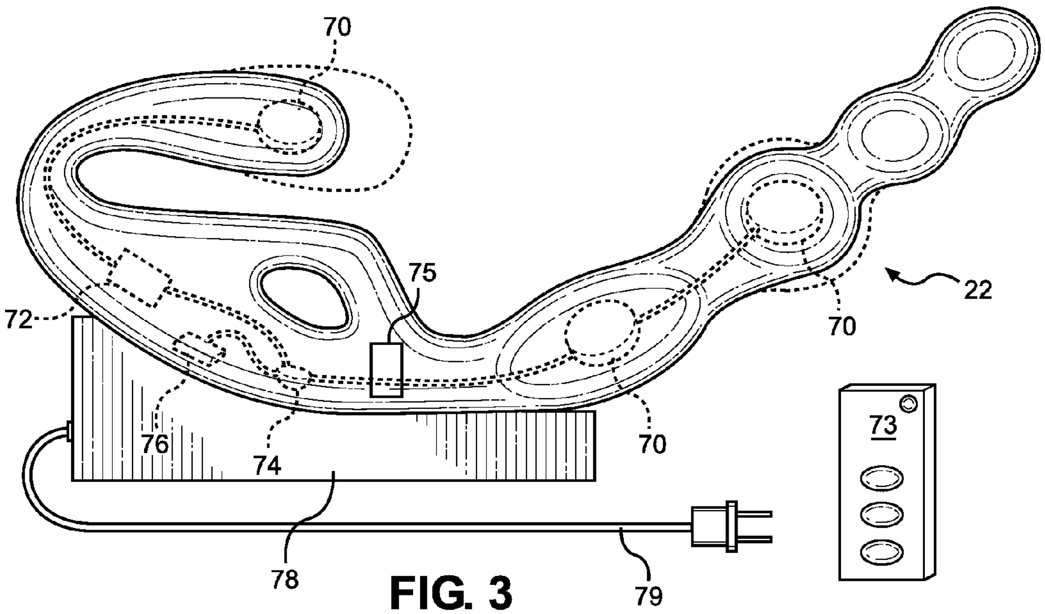

FIG. 3 (Sheet 2) illustrates a side view of a sex toy with internal vibrators and power system, in accordance with an embodiment of the present disclosure.

Figure 4:
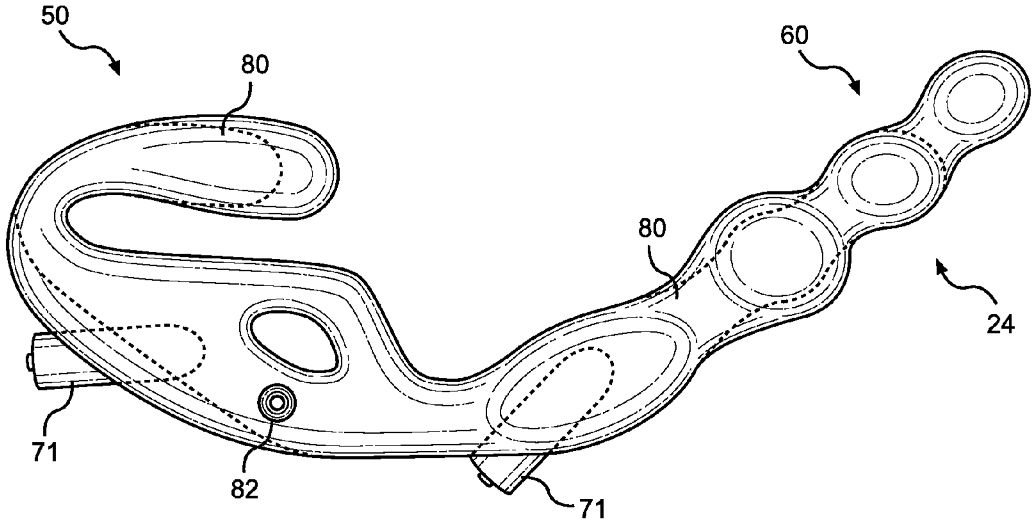

FIG. 4 (Sheet 2) illustrates a side view of a sex toy with external vibrators and an internal cavity, in accordance with an embodiment of the present disclosure.

Corresponding reference characters indicate corresponding components throughout the several figures of the Drawings. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiment are often not depicted in order to facilitate a less obstructed view of these various embodiments of the present disclosure.

REFERENCES

20 Sex toy
22 Water proof sex toy with internal vibrators
24 Sex toy with external vibrators and internal cavity
30 Cock ring
32 Cock ring vibrator
40 Fulcrum or "center region"
42 Point of attachment
44 Fulcrum region top surface
46 Height lowers where the sex toy could contact the wearer's testicles
50 Butt plug region or "rear region"
52 Proximate portion of the butt plug region
54 Distal portion of the butt plug region
60 Dildo region or "front region"
62 Space for wearer's testicles
64 Bulbous region
66 Proximate portion of the dildo region
68 Distal portion of the dildo region
70 Internal vibrator(s)
71 External vibrator(s)
72 Battery
73 Remote control
74 Control system
75 Manual Control
76 Power input
78 Cordless recharger
79 Power cord
80 Internal cavity
82 Valve

DETAILED DESCRIPTION

Preamble

The following description is not to be taken in a limiting sense, but is made merely for the purpose of describing the general principles of exemplary embodiments, many additional embodiments of this invention are possible. It is understood that no limitation of the scope of the invention is thereby intended. The scope of the disclosure should be determined with reference to the Claims. Reference throughout this specification to "one embodiment," "an embodiment," or similar language means that a particular feature, structure, or characteristic that is described in connection with the embodiment is included in at least one embodiment of the present disclosure. Thus, appearances of the phrases "in one embodiment," "in an embodiment," and similar language throughout this specification may, but do not necessarily, all refer to the same embodiment.

Further, the described features, structures, or characteristics of the present disclosure may be combined in any suitable manner in one or more embodiments. In the Detailed Description, numerous specific details are provided for a thorough understanding of embodiments of the disclosure. One skilled in the relevant art will recognize, however, that the embodiments of the present disclosure can be practiced without one or more of the specific details, or with other methods, components, materials, and so forth. In other instances, well-known structures, materials, or operations are not shown or described in detail to avoid obscuring aspects of the present disclosure. Any alterations and further modifications in the illustrated devices, and such further application of the principles of the invention as illustrated herein are contemplated as would normally occur to one skilled in the art to which the invention relates.

Unless otherwise indicated, the drawings are intended to be read (e.g., arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure would be seen by a perspective wearer of the sex toy looking down at it. Similarly, the terms "inwardly" and "outwardly" generally refer to the orientation of a surface relative to its axis of elongation, or axis of rotation, as appropriate. Also, as used herein, terms such as "positioned on" or "supported on" mean positioned or supported on but not necessarily in direct contact with the surface.

The phrases "at least one," "one or more," and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. The terms "a" or "an" entity refers to one or more of that entity. As such, the terms "a" (or "an"), "one or more" and "at least one" can be used interchangeably herein. It is also to be noted that the terms "comprising," "including," and "having" can be used interchangeably. Further, all numbers expressing dimensions, physical characteristics, and so forth, used in the specification and claims are to be understood as being modified in all instances by the term "about".

DESCRIPTION

For the purposes of promoting an understanding of the principles of the present invention, reference will now be made to the embodiments illustrated in the drawings and specific language will be used to describe the same.

As stated above, anal play for couples is fun, but it is difficult to simultaneously please both partners anally while also performing vaginal intercourse. Very generally, embodiments of the sex toy described herein comprise one end that is an anal dildo for a receiver and another end that is a butt plug for the wearer with a point of attachment between the two for the attachment of the sex toy to the wearer. In a preferred embodiment, the butt plug end is inserted into a man and a cock ring is strung through the point of attachment, which is a hole, and acts as a fulcrum and rotates the toy backwards slightly upon the thrust of the dildo end into the woman's anus, thereby transferring movement to the butt plug end up and against the man's prostate. Additionally, because the toy can be inserted in both partner's anuses simultaneously, each partner can directly feel a connection with the anal movements of the other partner.

It is anticipated that this design could also be used between female-female couples using a strap-on dildo, harness, or other means of attachment; in which case, the user of the strap-on dildo or harness would take the man's place in the description above. It is anticipated that this design could also be used between male-male couples, albeit more awkwardly. The toy could also be used without a cock ring, but it would be harder to hold in place.

Now referring to the drawings FIG. 1 illustrates a perspective view of one embodiment of a sex toy 20 with an attached cock ring 30. The sex toy 20 itself could be made of silicon, rubber, hard plastic, metal, glass, cyber skin, or any other material suitable to its purpose. The sex toy 20 could also be made of one solid piece or hollowed out entirely or only in certain portions. Methods of production are those of similar products in the market. Likewise, cock rings 30 are common in the market and can be made of silicon, rubber, hard plastic, metal, cyber skin, or any other material suitable to their purpose. A cock ring may also comprise an integrated or detachable vibrator 32.

From the perspective of a potential wearer of the sex toy 20, the sex toy is comprised of three primary regions which may create a generally hooked shape. The fulcrum region 40 is the center region and comprises one or more points of attachment 42 and serves to connect the two elongated, resilient, and generally cylindrical end regions sized for receipt in an anal or vaginal cavity. The end regions are: the butt plug region 50, which is a region in the rear, and the dildo region 60, which is in the front.

In the present embodiment the point of attachment 42 is a hole from one side of the sex toy to the other. In other embodiments the point of attachment could be a hole with a slot whereby a means for attachment, which could be a cock ring, strap, string, harness, rope, tether, fastener, leash, tie, band, strip, belt, bridle, halter, restraint, shackle, chain, Velcro or other means of attachment to a wearer could be removably slid into the hole such that the object for attachment is held securely. The point of attachment 42 need not be a hole. The point of attachment could be a point at which an integrated cock ring, strap, harness, rope, tether, fastener, leash, tie, band, strip, belt, bridle, halter, restraint, shackle, chain or other means of attachment to a wearer is permanently or detachably affixed with a ring, loop, hoop, circlet, snap, buckle, fastener, clip, latch, clasp, clutch, grip, clasp, staple, binder, button, press stud, crimp, tuck, fold, crease, lock, knot, Velcro or any other means of attachment known in the art.

The importance of the point of attachment is that it allows the wearer to attach the sex toy to their body, preferably their penis, thereby creating a pivot point or fulcrum for the butt plug 50 and dildo 60 regions of the sex toy 20 to move about;

thereby creating a suspended seesaw lever for the forces applied to either end region of the sex toy across the fulcrum and allowing more efficient transfer of kinetic energy allowing partners to experience the tiny tremors, clenches, and other movements of their partner, which in-turn creates a unique sensation of closeness.

Ideally, the object of attachment for a man would be a cock ring 30, as it attaches the sex toy in precisely the right location, tight against the wearer's perineum, and may also serve additional useful purposes. A leather cock ring that comes apart is ideal as it would easily be strung through a hole in the sex toy and removed again.

The fulcrum region 40 may be either narrower or wider in cross-section than either the butt plug 50 or dildo 60 regions, but should be wide enough as not to injure the wearer. The fulcrum region should ideally be sized so that its top surface 44 is flat and extends in length from the base of the penis to the anus for ideal placement of the butt plug region 50. Height wise, the fulcrum region 40 should lower 46 where the sex toy could contact the male gonads to prevent injury thereto, which is typically just forward of the point of connection 42. Either end of the fulcrum region 40 may be tapered toward the butt plug 50 and/or dildo 60 regions respectively.

Referring now to FIG. 2. FIG. 2 illustrates a side view of an embodiment of a sex toy with an attached cock ring. The rear end of the sex toy comprises a butt plug region 50, which extends upward and forward from a fulcrum region 40 and is intend to be inserted into a wearer's anus, or in rare cases, vagina. In a preferred embodiment, the dimensions of this region are ideally suited to stimulate a man's prostate while the sex toy 20 pivots about the point of attachment 42. The proximate portion 52 of the butt plug region may be tapered to increase the wearer's comfort while inserted anally and to allow for greater flexibility of the distal portion 54 of the region as the entire region moves around during intercourse. In a preferred embodiment, the entire butt plug region 50 is smooth; however, it is contemplated that the region may comprise one or more bulbous, knobbed, textured, or ridged sub-regions.

Still referring to FIG. 2, the front end of the sex toy 10 comprises a dildo region 60, which also extends upward and forward from a fulcrum region 40 and is intend to be inserted into the recipient's (not the wearer's) anus or vagina depending on their gender and sexual position. In a preferred embodiment, the length of this region is ideally sized to fill the anal cavity without pressuring the junction of the rectum and the sigmoid colon and will be longer than the butt plug region. The reason the dildo region is preferably longer than the butt plug region 50 is in order to provide appropriate space for a wearer's testicles 62 which would be located at the proximate end of the dildo region 66.

The dildo region 60, while elongated, resilient, and generally cylindrical; may be smooth; shaped like a penis; or may comprise one or more bulbous, knobbed, textured, or ridged sub-regions. In a prefer embodiment, the dildo region 60 may comprise one or more bulbous regions 64. In this preferred embodiment the bulbous regions would have a smaller diameter at the distal end of the dildo region 68 and would have wider diameters sequentially as they approach the proximate end of the dildo region 66, with the possible exception of the bulbous region under the space for the testicles 62 which could be smaller and somewhat flattened. The increasing diameter of the bulbous regions 64 would allow for the sex toy to be inserted into a recipient's anus in a graduated manner appropriate for a more relaxed penetration, while the variable diameters also facilitate the recipient's ability to grip the dildo region 60 of the sex toy 20 during use for increased stimulation. The ability to grip the dildo region 60 of the sex toy is of increased importance in this design because the point of attachment 42 and means for attachment create a fulcrum point for a leveraged seesaw like transfer of kinetic energy from the dildo region 60 to the butt plug 50 region of the sex toy.

Referring now to FIG. 3. FIG. 3 illustrates alternate embodiments of a sex toy without a cock ring attached. In one embodiment of a sex toy 22, the sex toy may be waterproof and comprise an internal vibrator 70, a rechargeable battery 72, a control system 74, and a power input 76. The internal vibrators 70 and control system 74 may be adapted to provide for variation in the duration and intensity of the vibration of the sex toy. The control system 74 may also be adapted to control the duration and intensity of vibration via a manual control 75 located on the sex toy or remotely via a separate wireless remote control 73. The rechargeable battery 72 may be recharged via a power input 76. The power input 76 may simply be a plug for a power cord, may be an electrically conductive plate designed to be paired with a cordless recharger 78, or may be any other method for conferring a charge to the battery.

A cordless recharger 78 may comprise a stand that holds the sex toy in a position such that each of the electrical leads on the cordless recharger come into contact with an electrically conductive plate on the sex toy. The electrically conductive plate may comprise a metallic disk which is one electrical lead and a metallic ring encircling the disk which is a second electrical lead, each of which pair with another electrical lead on a cordless recharger; such cordless charging systems for sex toys are already know in the art and are used in high-end waterproof sex toys. The cordless recharger 78 may then be plugged into a power socket with a power cord 79.

Referring now to FIG. 4. FIG. 4 illustrates alternate embodiments of a sex toy without a cock ring attached. In one embodiment of a sex toy 24, the sex toy may comprise one or more external vibrators 71 which may be removably inserted into said sex toy 24. In another embodiment a sex toy could have one or more internal cavities 80 in either the butt plug 50 region, dildo region 6, or running the length of the dildo region 60 of the sex toy to the butt plug region 50 of the sex toy. An internal cavity 80 may be filed with air or fluid. An internal cavity may also comprise one or more valves 82 whereby additional air or fluid may be added to or removed to said internal cavity.

In application, one region or another of the sex toy could be pumped up to a larger size. For example, an air valve could allow the butt plug region 80 to be pumped up to a larger size to provide greater pressure against the prostate, or so the butt plug region 80 would be less likely to slip out of the wearers body when in use. In another application, a fluid filled cavity would facilitate the ability of one user to squeeze their end of the sex toy while in use and create a corresponding increase in size and pressure on the other end of the sex toy for the other partner. FIG. 3 illustrates possible changes in dimensions of the corresponding ends when filled with fluids in dashed lines.

CONCLUSION

Information as herein shown and described in detail is fully capable of attaining the above-described object of the present disclosure, the presently preferred embodiment of the present disclosure; and is, thus, representative of the subject matter; which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above described preferred embodiment and additional embodiments as regarded by those of ordinary skill in the art are hereby expressly incorporated by reference and are intended to be encompassed by the present claims.

What is claimed is:

1. A sex toy for use by two partners, comprising:

(a) a first elongated, resilient, and generally cylindrical rear end region sized for receipt in an anal or vaginal cavity having proximate and distal end portions;

(b) a second elongated, resilient, and generally cylindrical front end region sized for receipt in an anal or vaginal cavity having proximate and distal end portions;

(c) a center region wherein said first and said second end regions connect on opposing sides; and (d) a point of attachment for an attachment capable of going around a penis on said center region.

2. The apparatus of claim 1, further comprising a means for an attachment capable of going around a penis.

3. The apparatus of claim 2, wherein said means for attachment and said point of attachment create a fulcrum or pivot point for transferring kinetic energy from one of said ends to the other.

4. The apparatus of claim 2, wherein said means for attachment is a cock ring.

5. The apparatus of claim 4, wherein said a cock ring also comprises a vibrator.

6. The apparatus as set forth in claim 2, wherein said point of attachment comprises a hole through said center region for said means capable of attachment around a penis.

7. The apparatus of claim 1, wherein said rear end region is sized for receipt in an anal cavity and extends above and forward in a hook like fashion from where it attaches to the center region.

8. The apparatus of claim 1, wherein said front-end region further comprises one or more bulbous regions.

9. The apparatus of claim 1, wherein said front-end region is phallic shaped with an enlarged tip.

10. The apparatus of claim 1, further comprising a vibrator.

11. The apparatus of claim 10, wherein said sex toy is waterproof.

12. The apparatus of claim 10, wherein said vibrator can be removably inserted into said sex toy.

13. The apparatus of claim 10, wherein said vibrator is internal to said sex toy.

14. The apparatus of claim 10, further comprising a power input that is an electrically conductive plate that can pair with a cordless recharger.

15. The apparatus of claim 10, further comprising a control system for said vibrator that regulates duration and intensity of vibration.

16. The apparatus of claim 15, further comprising a remote control that controls said control system.

17. The apparatus of claim 1, wherein said sex toy further comprises an internal cavity.

18. The apparatus of claim 17, further comprising a valve, wherein the pressure in said cavity may be increased or decreased by use of said valve.

19. The apparatus of claim 17, wherein said internal cavity contains a fluid.

* * * * *